United States Patent [19]

Matsuo et al.

[11] Patent Number: 4,622,978

[45] Date of Patent: Nov. 18, 1986

[54] ULTRASONIC DIAGNOSING APPARATUS

[75] Inventors: Satoshi Matsuo; Yasuo Miyajima, both of Ootawara, Japan

[73] Assignee: Kabushiki Kaisha Toshiba, Kawasaki, Japan

[21] Appl. No.: 677,852

[22] Filed: Dec. 4, 1984

[30] Foreign Application Priority Data

Dec. 5, 1983 [JP] Japan ................................. 58-230187

[51] Int. Cl.$^4$ .............................................. A61B 10/00
[52] U.S. Cl. ........................................ 128/663; 73/626
[58] Field of Search ...................... 128/663; 73/861.25, 73/626

[56] References Cited

U.S. PATENT DOCUMENTS

| 4,182,173 | 1/1980 | Papadofranvgakis et al. ...... 128/663 X |
| 4,370,985 | 7/1983 | Takeichi .............................. 128/663 |
| 4,373,533 | 2/1983 | Iinuma ................................ 128/663 |
| 4,407,293 | 10/1983 | Suarez, Jr. et al. ............. 128/663 X |
| 4,413,629 | 11/1983 | Durley, III ........................ 128/660 |
| 4,492,120 | 1/1985 | Lewis et al. ....................... 128/663 |
| 4,509,525 | 4/1985 | Seo ................................... 128/660 X |
| 4,509,526 | 4/1985 | Barnes et al. ..................... 128/663 |
| 4,530,363 | 7/1985 | Brisken .............................. 128/663 |

OTHER PUBLICATIONS

Marich, K. W. et al., "An Improved Uts Imaging System", Uts Imaging 3, #4 pp. 309-322 Oct. 1981.
Arenson, J. W. et al., "A Linear Stepped Doppler Uts Array", Conf. 1980, Uts Symp. Proceedings, Boston, Mass. Nov. 5-7, 1980, pp. 775-779.

Primary Examiner—Kyle L. Howell
Assistant Examiner—Francis J. Jaworski
Attorney, Agent, or Firm—Finnegan, Henderson, Farabow, Garrett & Dunner

[57] ABSTRACT

An ultrasonic diagnosing apparatus transmits an ultrasonic wave into a subject under examination, thereby obtaining a tomogram and blood flow information of the subject. This ultrasonic diagnosing apparatus is equipped with an ultrasonic probe provided with a transducer array, in which a plurality of ultrasonic transducer elements are arranged, and a Doppler transducer independent of this transducer array, and switching devices for switching the operation mode of a transmitter/receiver system of the transducer array of this ultrasonic probe. The transducer array is used for transmission and reception of the ultrasonic wave when obtaining a tomogram and is used for either the transmission or reception of a continuous ultrasonic wave when obtaining blood flow information. The Doppler transducer is used for either the transmission or reception of the continuous ultrasonic wave only when obtaining the blood flow information.

21 Claims, 6 Drawing Figures

ULTRASONIC DIAGNOSING APPARATUS

BACKGROUND OF THE INVENTION

The present invention belongs to the field of medical diagnosis using an ultrasonic wave and, more particularly, it relates to an ultrasonic diagnosing apparatus in which a tomogram of a subject under examination is obtained due to a pulse-echo method, and blood flow information is derived due to a continuous wave Doppler method.

A Doppler ultrasonic method which is used to obtain blood flow informatioin is mainly classified into a modulated wave Doppler method using the modulated (amplitude modulated) ultrasonic wave and a continuous wave Doppler method using a continuous wave of the ultrasonic wave.

A typical modulated wave Doppler method is a pulsed Doppler method. In the pulsed Doppler method, a pulsed ultrasonic wave forming a burst wave having a pulse-like envelope is sent into a subject under examination, and the blood flow information is measured from an echo component (returned component) due to the reflection of the ultrasonic wave by (a hemocyte of) a blood flow. This blood flow information is measured by measuring the influence due to the Doppler effect in the echo component. Advantages of this pulsed Doppler method include the possibility of commonly using a probe and a transmitter/receiver in a tomograph to obtain an ultrasonic tomogram (B mode image) by the pulse-echo method (since a pulsed wave is used in both pulsed Doppler method and pulse-echo method), and the blood flow information at an arbitrary position on the tomogram is derived, etc.

However, in the modulated wave Doppler method, there is a limitation in principle regarding the detection range of the blood flow velocity, and it is difficult to identify a high blood flow velocity. Namely, first, the frequency deviation of only up to half of the repetition frequency of the ultrasonic pulse can be accurately detected according to this modulated wave Doppler method. Therefore, it is impossible to measure the blood flow velocity exceeding the velocity corresponding to the above frequency deviation. Second, according to the modulated wave Doppler method, when measuring the blood flow velocity at a portion in a particular depth of a subject, the cyclic period of the ultrasonic pulse cannot be shorter than the time the ultrasonic wave travels to that depth and back to the transducer. Because of these reasons, it is difficult to identify a high blood flow velocity.

On the other hand, in the continuous wave Doppler method, a non-modulated continuous ultrasonic wave is sent into a subject and blood flow information is obtained on the basis of the echo signal received by another transducer other than a transducer used for transmission of a wave; therefore, there is not such a limitation regarding the detection range as mentioned above.

However, the continuous wave Doppler method needs independent transducers for transmitting and receiving a wave, respectively, so that the arrangement becomes complicated. Further, in the continuous wave Doppler method, since a continuous wave is used, the resolution is not provided with respect to the distance from the transducers for transmission and reception, that is, with regard to the direction along the ultrasonic beam, so that it is difficult to identify the measuring position.

As an ultrasonic probe used in the continuous wave Doppler method, for example, there is known a type such as shown in U.S. Pat. No. 4,413,629. FIG. 1 schematically shows an ultrasonic probe of this type. An ultrasonic probe 1 has a transmitting transducer 2 and a receiving transducer 3 which are respectively fixed at the distal end.

However, since the transducers 2 and 3 of the probe 1 are fixed, the measuring areas which are determined due to the directivity of the transducer 2 for transmission and due to the directivity of the transducer 3 for reception are fixed. Namely, the measuring area is the intersecting area of the transmission beam from the transducer 2 for transmission and the receiving beam of the transducer 3 for reception. (The ultrasonic wave which is received can be regarded as a ultrasonic beam since the transducer has wave-reception directivity. This particular ultrasonic beam is called the receiving beam.) When the transducers 2 and 3 are fixed, both beam positions to the probe 1 are fixed, so that the intersecting area of both beams is fixed. Therefore, when using this probe 1, a plurality of probes which were respectively set to various distances between the probe and the measuring area are preliminarily prepared, and the probe in accordance with the depth of the measuring position must be selected from among these plurality of probes and has to be used. In addition, the probe for the measurement of the blood flow due to this Doppler method is constituted separately from (quite irrespectively and independently of) a transducer array for a tomogram (not shown) to obtain tomograms; therefore, there are drawbacks such that it is difficult to comprehend the corresponding relation with the tomograms, and it is also difficult to clearly discriminate from which portion in a subject under examination the measured blood flow information was obtained, and the like.

On the other hand, an ultrasonic probe 4 as shown in FIG. 2 is considered. A transducer array 5 for picking up tomograms, a single transducer 6 for transmitting a continuous wave for measuring the blood flow due to the Doppler method, and a single transducer 7 for receiving this continuous wave are respectively fixed to the point of the probe 4. In the transducer array 5, a plurality of transducer elements are arranged in a line. Such a probe can relatively easily grasp the corresponding relation with the tomograms. However, since there is a limitation regarding the overall size of the probe 4, mainly in consideration of the easiness of use, there is a tendency such that the areas of the transmission surface of the transducer 6 and of the reception surface of the transducer 7 become insufficient. In such a case, the sensitivities of the transducers 6 and 7 deteriorate, so that accurate blood flow information cannot be obtained. On the other hand, similar to the case of the probe 1 shown in FIG. 1, since both transducers 6 and 7 are fixed, the intersecting area of the transmitting beam and receiving beam is fixed, so that it is impossible to obtain stable sensitivity from a shallow portion to a deep portion in the subject.

SUMMARY OF THE INVENTION

It is an object of the present invention to provide an ultrasonic diagnosing apparatus in which both tomogram and blood flow information can be obtained, and the accurate blood flow information can be derived while identifying the position of the measuring portion of the blood flow information on the tomogram, and at the same time, with respect to the measurement of blood flow information, a good sensitivity can be obtained irrespective of the depth of the measuring portion in a subject under examination.

In an ultrasonic diagnosing apparatus according to the present invention, an ultrasonic wave is transmitting into a subject under examination, thereby obtaining the tomogram and blood flow information of the subject. The ultrasonic diagnosing apparatus is equipped with: an ultrasonic probe, provided with a transducer array in which a plurality of ultrasonic transducer elements are arranged and a Dopper transducer which consists of an ultrasonic transducer independent of this trasducer array; and a switching device for switching the operation mode of a transmitter/receiver system of the transducer array of this ultrasonic probe. The transducer array is used to transmit/receive an ultrasonic wave when obtaining a tomogram and is used to either transmit or receive a continuous ultrasonic wave when obtaining blood flow information. The Doppler transducer provided in the same ultrasonic probe as this transducer array is used to either receive or transmit the continuous ultrasonic wave only when the blood flow information is derived. That is, only the transducer array is used for transmission/reception of a pulsed ultrasonic wave when obtaining the tomogram. On the other hand, a Doppler transducer and a transducer array are used for transmission and reception of the continuous ultrasonic wave in the case of obtaining the blood flow information. The operation of the transducer array is changed over by switching the operation mode of the transmitter/receiver system of the transducer array in response to a control signal which is output from a control signal generating section.

According to the invention, the transducer array and Doppler transducer are attached to the same probe and either the transducer array or Doppler transducer is used for transmission, and the other is used for reception when the blood flow information is obtained. The directivity (transmission directivity or reception directivity) of the transducer array can be changed due to an electrical control, thereby enabling the direction of the transmission beam or receiving beam to be changed in measuring the blood flow information. Due to this change of the beam direction, the position of the intersecting area of the transmission beam and receiving beam is changed and the depth of the measuring portion is adjusted, so that the optimum receiving sensitivity can be derived with regard to an arbitrary depth in a subject under examination. Therefore, with respect to an arbitrary portion in a subject, the accurate blood flow information can be measured while identifying the measuring portion on the tomogram. In addition, since the transducer array to obtain tomograms and the transmitter/receiver system are also used in the case of obtaining the blood flow information, there is a useful construction and the overall apparatus can be miniaturized.

DETAILED DESCRIPTION OF THE PREFERRED EMBODIMENTS

Figure 1:
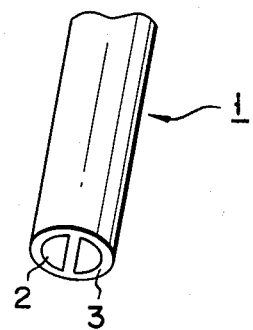
FIGS. 1 and 2 are explanatory diagrams showing ultrasonic probes which have been conventionally used, respectively.
Figure 2:
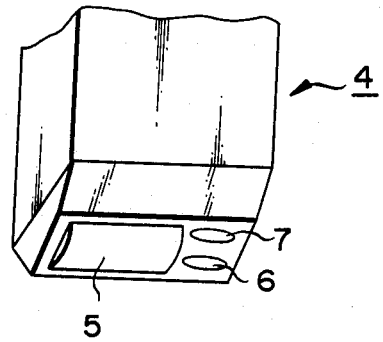
Figure 3:
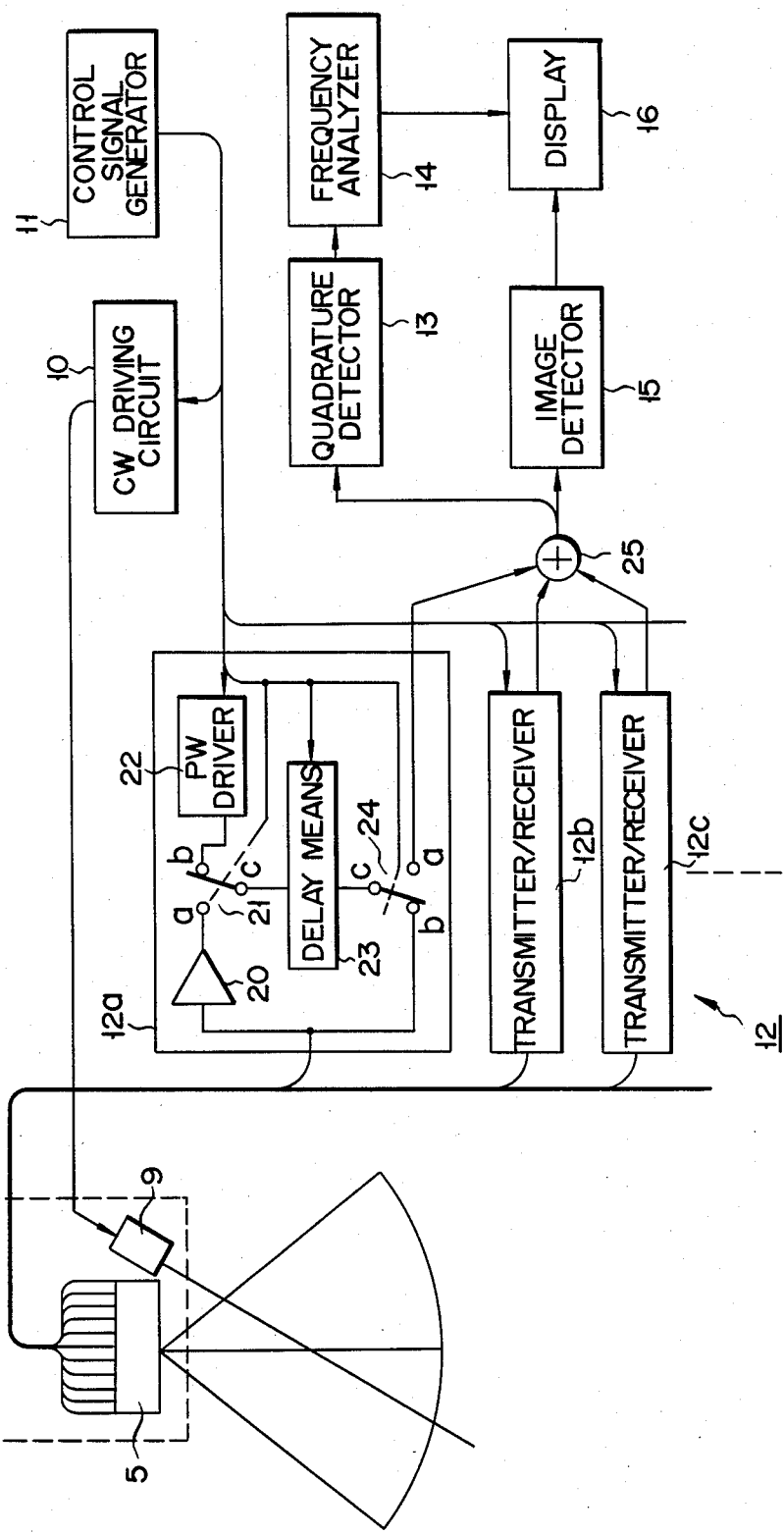
FIG. 3 is a block diagram showing an arrangement of an ultrasonic diagnosing apparatus according to a first embodiment of the invention.

In an ultrasonic diagnosing apparatus according to the first embodiment of the invention shown in FIG. 3, a sector scanning system is adopted to obtain a tomogram.

A Doppler transducer 9 consisting of at least one transducer element and the transducer array 5, in which a plurality of transducer elements are arranged in a line and which is used as a phased array, are attached to the distal end of an ultrasonic probe 27.

The Doppler transducer 9 is used only to transmit a continuous ultrasonic wave when a blood flow is measured. The transducer array 5 is used to receive the continuous ultrasonic wave transmitted from the transducer 9 for transmission when obtaining blood flow information and to transmit and receive a modulated ultrasonic wave, for example, a pulsed wave when obtaining a tomogram of a subject under examination (not shown).

A control signal to control the operation of a CW (continuous wave) driving circuit 10 is output from a control signal generator 11, and at the same time a control signal to control the operation of a transmitting-/receiving section 12 consisting of a plurality of transmission/receivers 12a, 12b, 12c . . . is also outputted.

The CW driving circuit 10 is made operative in response to the control signal which is given from the control signal generator 11, and a CW drive signal is supplied to the Doppler transducer 9 from the CW driving circuit 10. This CW drive signal is the electrical signal for driving the Doppler transducer 9, thereby allowing a stable continuous ultrasonic wave to be generated. The transmitting/receiving section 12 (the detailed arrangement will be explained later) is also made operative in response to the control signal which is given from the control signal generator 11. Each of the transmitters/receivers 12a, 12b . . . in the transmitting-/receiving section 12 is connected to each element in the transducer element 5, respectively. On the other hand, these transmitters/receivers 12a, 12b, . . . are also connected to an adder 25. The transmitters/receivers 12a, 12b . . . are used for transmission/reception of the ultrasonic waves through the transducer array 5. Each of the transmitter/receivers 12a, 12b . . . has a function to drive each element in the transducer array 5 in response to the control signal which is sent from the control signal generator 11 and thereby to allow a modulated wave, namely, a pulsed ultrasonic wave to be transmitter, a function to supply a received echo signal responsive to the signal from each element in the transducer array 5 to the adder 25, and a function to selectively make both of these functions effective in response to the control signal from the control signal generator 11.

The adder 25 additionally synthesizes outputs of the transmitters/receivers 12a, 12b, and the result of the addition is selectively supplied from the adder 25 to a guadrature detecting circuit 13 for phase detection and to an image detecting circuit 15. The quadrature detector 13 obtains the phase detected outputs of two phases of the received signal in which there is the phase difference of 90°. The image detector 15 includes a circuit to detect the amplitude change, i.e., envelope of the output signal of the adder 25, and a circuit to logarithm compress the detected signal from the above envelope detector and the like and produces a signal necessary for display of a tomogram.

The quadrature detector 13 detects the phase of the output signal of the adder 25 when obtaining the blood flow information. The output of the quadrature detector 13 is input to a frequency analyzer 14 to perform the frequency analysis using, for instance, the FFT (fast Fourier transform) method, so that a frequency deviation due to the Doppler effect, i.e., a magnitude of the Doppler shift, is analyzed. The result of the analysis by the frequency analyzer 14 is given to a display 16, and the blood flow information is displayed.

When a tomogram of a subject under examination is derived, the image detector 15 detects from the output signal of the adder 25 the information of the ultrasonic wave reflected by a tissue in the subject, which is necessary for display of the tomogram. The output of the image detector 15 is supplied to the display 16 and the tomogram is displayed.

The detailed arrangement of the transmitters/receivers constituting the foregoing transmitting/receiving section 12, for instance, the arrangement of the transmitter/receiver 12a will now be explained. This transmitter/receiver 12a comprises: a PW driver 22 for generating a PW (pulsed wave) drive signal as an electrical signal to vibrate one of the transducer elements in the transducer array 5 and thereby to allow a pulsed ultrasonic wave as a modulated ultrasonic wave to be radiated in response to the control signal given from the control signal generator 11; switching means, for example, electronic switches 21 and 24, for switching the transmission mode/reception mode of the ultrasonic wave in response to the control signal given from the control signal generator 11; an amplifier 20 for amplifying an electrical signal, i.e., echo signal, output from the transducer array 5 when the ultrasonic wave echo reflected by a tissue in the subject is received; and delay means 23 for delaying by a predetermined delay time the PW drive signal output from the PW driver 22 and transmitted and the echo signal output from the amplifier 20 after reception. The other transmitters/receivers 12b, 12c . . . are constituted in a similar manner as the transmitter/receiver 12a.

The operation of the ultrasonic diagnosing appartus constituted as described above will now be explained.

First, the case where a tomogram, i.e., B mode image of a subject under examination, is derived by this ultrasonic diagnosing apparatus will be described.

In this case, the operation mode of the transmitting/receiving section 12 is alternately switched to the transmission mode and reception mode in response to the control signal (e.g., repetitive pulse signal which repeats at every predetermined time period) output from the control signal generator 11. The transmission mode denotes the state whereby respective common contacts c of the electronic switches 21 and 24 are connected to each corresponding contact b in response to the control signal from the control signal generator 11, so that the PW drive signal output from the PW driver 22 can be input to each corresponding transducer element in the transducer array 5 through the delay means 23. On the other hand, the reception mode means the state whereby the respective common contacts c of the electronic switches 21 and 24 are connected to each corresponding contact a in response to the control signal from the control signal generator 11, so that the echo signal output from the amplifier 20 can be input to the adder 25 through the delay means 23.

The transmitters/receivers 12a, 12b . . . operate as follows when they are in the transmission mode. Namely, the PW drive signal which is output from the PW driver 22 is supplied through the delay means 23 to each transducer element constituting the transducer array 5. Each transducer element is vibrated in response to the PW drive signal. The ultrasonic wave is transmitted into the subject (tissue) due to the vibration of the transducer element. The directivity in transmission of this ultrasonic wave, namely, the directivity of the transmission beam, is determined by the delay time of the delay means 23 which is respectively provided in each of the transmitters/receivers 12a, 12b. . . The delay time of the delay means 23 can be controlled by the control signal generator 11.

The ultrasonic wave transmitted into the subject in this way is reflected by a tissue in the subject. This reflected ultrasonic wave, i.e., ultrasonic echo, is received by the transducer array 5 and converted to the electrical signal; thereafter, it is input as the echo signal to each of the transmitters/receivers 12a, 12b . . . for every channel. At this time, the respective transmitters/receivers 12a, 12b . . . are switched to the reception mode.

The echo signal input to each of the transmitters/receivers 12a, 12b . . . is amplified by the amplifier 20 provided in each of the transmitters/receivers 12a, 12b . . . Each output of the amplifiers 20 is further delayed by a predetermined delay time by the delay means 23 is a manner such that a predetermined reception directivity is shown, then those delayed outputs are give to the adder 25 and are added and synthesized.

From the synthetic echo signal added by the adder 25, the component necessary for display of a tomogram is detected and extracted by the image detector 15. The detected output of the image detector 15 is supplied to the display 16, and the tomogram is displayed.

Next, the case where the blood flow information of a subject under examination is derived by this ultrasonic diagnosing apparatus will be described. In this ultrasonic diagnosing apparatus, the blood flow information of the subject is obtained using the continuous wave Doppler method.

That is, the CW drive signal is output from the CW driver 10 in response to the control signal output from the control signal generator 11, and at the same time, each of the transmitters/receivers 12a, 12b . . . in the transmitting/receiving section 12 is fixed into the reception mode (the common contacts c of the electronic switches 21 and 24 are connected to each corresponding contact a).

When the CW drive signal is output from the CW driver 10, a continuous ultrasonic wave is transmitted into the subject from the Doppler transducer 9 in response to this CW drive signal. The transmitted ultrasonic wave is scattered by hemocyte in the blood in the subject, and the ultrasonic echo including these scattered components is received by each transducer element in the transducer array 5, so that it is converted to the electrical signal as the echo signal. The echo signal output from each transducer element in the transducer array 5 is input to the transmitter/receivers 12a, 12b . . . in the transmitting/receiving section 12, respectively (as already mentioned before, the transmitters/receivers 12a, 12b . . . are fixed into the reception mode, respectively).

The echo signal inputted to each of the transmitters/receivers 12a, 12b and 12c is amplified by teh amplifiers 20 respectively provided in the transmitters/receivers 12a, 12b and 12c; furthermore, it is delayed by the delay means 23 in such a manner that predetermined reception directivities are shown, and thereafter the delayed echo signals are added and synthesized by the adder 25.

The frequency deviation information of the echo signal added by the adder 25 is fetched (phased detected) in the quadrature detector 13, and this frequency deviation information is supplied to the frequency analyzer 14, thereby performing the frequency analysis. This analysis result is given to the display 16 and is displayed as the blood flow information.

Figure 4:
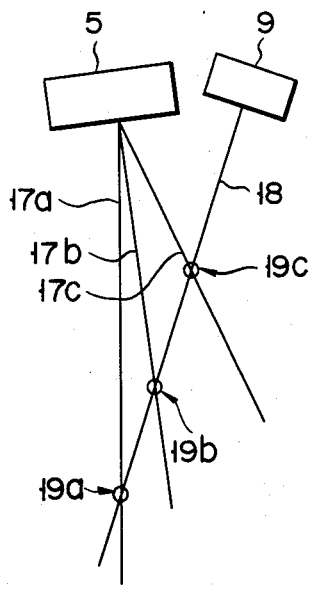
FIG. 4 is a diagram for explaining the operation of the ultrasonic diagnosing apparatus shown in FIG. 3.

Next, the relation between the continuous ultrasonic wave transmitted into the subject and the received wave of the ultrasonic echo scattered in the subject will be explained with reference to FIG. 4. In case of the sector scanning type due to the electron scan as in this apparatus, by changing over the delay time of each of the tramsitters/receivers 12a, 12b . . . (this delay time is switched responsive to the control signal output from the control signal generator 11), the reception directivity of the transducer array 5 can be changed in such a manner that receiving beams (which are virtual acoustic beams corresponding to the substantial sensitivity distribution formed as the result of the reception of the ultrasonic wave as already described before, and in the apparatus in this embodiment, as the result of the signal process, the acoustic component regarding only the relevant direction is selectively received and processed as if such beams entered.) 17a, 17b and 17c as shown in, e.g., FIG. 4 are formed. The change in reception directivity denotes that (the position of) the cross point of a transmission beam 18, responsive to the transmission directivity of the Doppler transducer 9 and the receiving beam of the transducer array 5, is changed (cross points 19a, 19b and 19c are formed in correspondence to the receiving beams 17a, 17b and 17c, respectively). Due to this operation, the depth of the measuring portion on the receiving sensitivity in the subject is changed. Therefore, by changing the delay time of the delay means 23 provided in each of the transmitters/receivers 12a, 12b, 12c . . . due to, for instance, the switching operation by the operator (practically speaking, the delay time can be changed by controlling the delay means 23 through the control signal generator 11 by external switching means (not shown) which is made operative in response to, e.g., the operation by the operator), the position at which the maximum receiving sensitivity is obtained is adjusted, so that this makes it possible to obtain the optimum receiving sensitivity corresponding to the depth of the portion which should be measured in the subject.

As described above, in this ultrasonic diagnosing apparatus which can measure a subject with the optimum measuring sensitivity irrespective of the depth in the subject, the influence due to an unnecessary signal (clutter, i.e., a signal from other moving tissues than the hemocytes in an organism in this case) can be effectively reduced; therefore, the very accurate blood flow information can be derived.

The invention is not limited to only this embodiment but can be implemented by suitably modifying the embodiment within the purview which is substantially included in the spirit of the invention.

For example, in the first embodiment of the invention, the invention has been applied to the ultrasonic diagnosing apparatus adopting the sector scanning system in the image pick-up of a tomogram. However, the invention can be also applied to an ultrasonic diagnosing apparatus adopting another scanning system.

For instance, the second embodiment whereby the invention was applied to an ultrasonic diagnosing apparatus adopting a linear scanning system will be explained with reference to FIG. 5.

Figure 5:
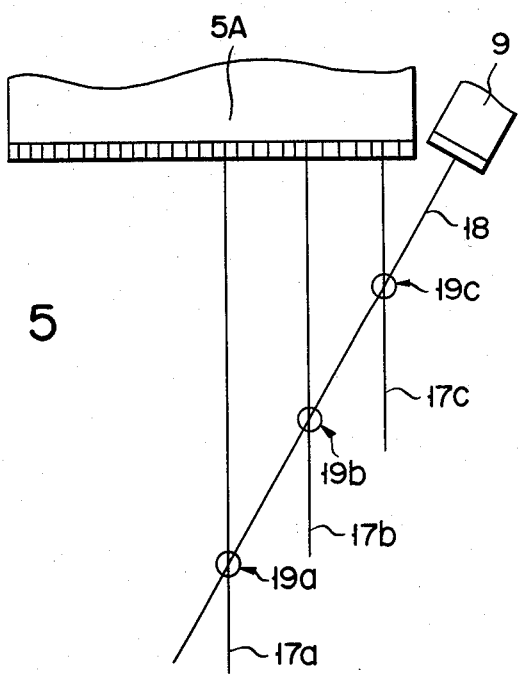
FIG. 5 is a diagram for explaining the operation of an ultrasonic diagnosing apparatus according to a second embodiment of the invention.

As is well known, in the linear scanning system, at least one (a few elements in many cases) of a plurality of transducer elements constituting a transducer array 5A shown in FIG. 5 is driven, so that an ultrasonic beam is radiated in a particular direction. Further, one or a plurality of transducer elements which are driven are switched by at least one element at a time by switching means, e.g., electronic switch, thereby allowing the ultrasonic beam to be moved substantially in parallel and the scan to be performed. At this time, the reflected acoustic wave is received in a manner such that the echo signal is taken in from one or a plurality of transducer elements substantially corresponding to that used for transmission.

In this second embodiment, therefore, the transducer array 5A is used for reception of the wave, and the echo signal received by the transducer array 5A is taken in from one or a plurality of transducer elements, and at the same time, the transducer in which this echo signal is taken is selectively switched by the switching means, thereby allowing the reception directivities (indicated by the receiving beams 17a, 17b and 17c) to be changed. In this way, the reception directivity of the transducer array 5A is controlled, so that the positions of the cross points 19a, 19b and 19c between these receiving beams 17a, 17b and 17c and the transmission beam 18 are changed. The depth of the measuring portion on the reception sensitivity in the subject is changed due to such control of the reception directivity of the transducer array 5A.

Consequently, similarly to the first embodiment, by controlling the reception directivity of the transducer array 5A due to the operation by the operator, this apparatus can be adjusted so that the optimum reception sensitivity in accordance with the portion that should be measured in the subject is obtained. Therefore, even in the apparatus in this embodiment, the blood flow information is measured with the optimum reception sensitivity, and the very accurate blood flow information is derived irrespective of the depth in the subject. In addition, the arrangements of the circuits and the like of the apparatus are not shown in particular, but they are almost schematically similar to the arrangements in the first embodiment shown in FIG. 3. It will be obviously understood that the same transmitter/receiver can be commonly used in both cases where the tomogram is obtained and where the blood flow information is derived.

Figure 6:
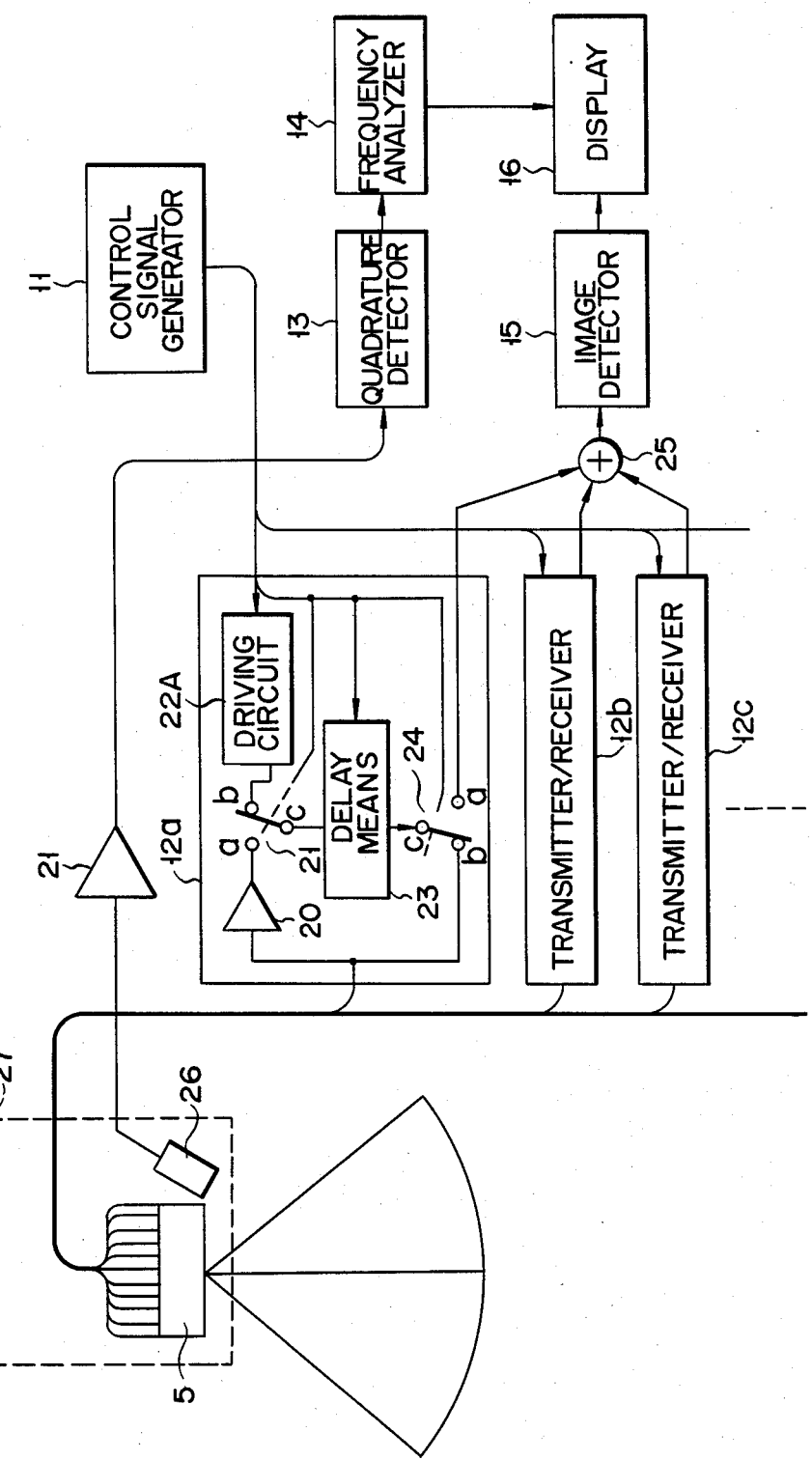
FIG. 6 is a block diagram showing an arrangement of an ultrasonic diagnosing apparatus according to a third embodiment of the invention.

On one hand, the transducer arrays 5 and 5A have been used for reception of the wave when the blood flow information is obtained in the first and second embodiments; however, the transducer arrays 5 and 5A may be used for transmission. Next, the third embodiment of an example in the case of an ultrasonic diagnosing apparatus of the sector scanning type similar to the first embodiment will be explained with reference to FIG. 6. In FIG. 6, the components and elements designated by the same reference numerals as those in FIG. 3 have the substantially same functions as the corresponding components and elements in FIG. 3.

Different points between the apparatuses in FIGS. 6 and 3 are that, in the ultrasonic diagnosing apparatus shown in FIG. 6, the CW driver 10 is not provided, since the transducer array 5 is used for transmission when the blood flow information is measured, a driving circuit 22A in the transmitter/receiver 12a is constituted so that it can output not only the PW drive signal but also the CW drive signal, and the echo signal received by a Doppler transducer 26 for reception is input to the quadrature detector 13 through the amplifier 21.

In case of obtaining the blood flow information by the ultrasonic diagnosing apparatus shown in FIG. 6, the transmitters/receivers 12a, 12b . . . are set into the trasnmission mode (the common contacts of the electronic switches 21 and 24 are connected to each corresponding contact a), so that the CW drive signal is output from the PW driving circuit 22A. In this case, the driving circuit 22A has the function to generate an ultrasonic drive signal corresponding to the CW drive signal and to modulate this drive signal and output it as, e.g., the PW drive signal. In this driving circuit 22A, when the ultrasonic drive signal is output without being modulated, this output becomes the CW drive signal. The CW drive signal output mode of the driving circuit 22A is set interlockingly when the transmitters/receivers 12a, 12b . . . are set into the transmission mode in response to the control signal output from the control signal generator 11.

The CW drive signal output from the driving circuit 22A is appropriately delayed for every channel by the delay means 23 and is subjected to the excitation (which means the transmission of the continuous ultrasonic wave) of the transducer array 5. The delay time in every channel by the delay means 23 and its combination correspond to the transmission directivity.

On the other hand, the ultrasonic wave scattered in the subject is received by the Doppler transducer 26 and converted to the electrical signal. After this electrical signal was amplified by the amplifier 21, it is phase detected by the quadrature detector 13.

In this case, by changing the delay time of the delay means 23 and by changing the transmission directivity, the apparatus can be adjusted so that the optimum measuring sensitivity is obtained in accordance with the depth of the portion that should be measured in the subject. This is because if the transmission directivity changes, the position of the cross point between the transmission beam and the receiving beam will vary.

The operation to obtain a tomogram is almost similar to that in the case of FIG. 3; therefore, it is omitted.

As described above, even in the case where the transducer array 5 for examination of a tomogram is used for transmission, a similar effect as in the first embodiment can be also obtained.

In the ultrasonic diagnosing apparatus of the linear scanning type described in the second embodiment, similar to the third embodiment, it is also obviously possible to transmit an ultrasonic wave from the transducer array for examination of a tomogram when the blood flow information is measured by a continuous wave and to use the Doppler transducer only for reception.

Also, in general, the ultrasonic transducer can be utilized for both transmission and reception. The same transducer may be also applied as the Doppler transducer 9 in FIG. 3 and as the Doppler transducer 26 in FIG. 6.

Although the Doppler transducer 9 in FIG. 3 and the Doppler transducer 26 in FIG. 6 may be constituted by the single transducer element or by a plurality of transducer elements, the transducer in which a relatively sharp single directivity is obtained is suitable.

What is claimed is:

1. An ultrasonic measuring apparatus for determining information concerning the blood flow of a living subject to be examined comprising:
   a transducer probe for contact with the exterior surface of the subject;
   Doppler transducer means, mounted on said transducer probe, for transmitting a continuous ultrasonic wave toward the subject along a fixed, first beam for intersection with the blood flow within the subject;
   a transducer array of ultrasonic elements, mounted on said transducer probe proximate said Doppler transducer means, for receiving ultrasonic echos of the continuous ultrasonic wave which are reflected from the blood flow along a variable, second beam which intersects said first beam at an intersection point located within the blood flow of the subject;
   scanning means, coupled with said transducer array, for selectively varying the direction of said second beam to adjust the intersection point of said first and second beam and thereby adjust the depth of the intersection point within the subject;
   processing means, coupled with said Doppler transducer means and said transducer array, for processing signals from said Doppler transducer and said transducer array to provide a signal indicative of the velocity of the blood flow within the subject at the intersection point; and
   indication means, coupled with said processing means, for providing an output of information indicative of the velocity of the blood flow within the subject at the intersection point.

2. The ultrasonic apparatus of claim 1 wherein said transducer array is a plural array having a single central axis perpendicular to the array face and wherein said Doppler transducer probe and said transducer array are fixedly mounted on said trasnducer probe so that the first, fixed beam of the Doppler transducer probe and the single, central axis of the transducer array point in different directions.

3. The ultrasonic measuring apparatus of claim 1 wherein said indication means includes displaying means for visually displaying the velocity of blood flow.

4. The ultrasonic measuring apparatus of claim 1 wherein said scanning means includes means for steering said second beam by controlling the timings of exciting the ultrasonic elements of said transducer array.

5. The ultrasonic measuring apparatus of claim 1 wherein said scanning means includes means for translating said second beam by changing the ultrasonic elements of said transducer array to be excited along the array.

6. The ultrasonic measuring apparatus of claim 1 wherein said process means includes a quadrature detector.

7. The ultrasonic measuring apparatus of claim 6 wherein said process means further includes a Fourier transform analyzer.

8. An ultrasonic measuring apparatus for determining information concerning the blood flow of a living subject to be examined comprising:

a transducer probe for contact with the exterior surface of the subject;

a transducer array of ultrasonic elements, mounted on said transducer probe, for transmitting a continuous ultrasonic wave toward the subject along a variable, first beam for intersection with the blood flow within the subject;

Doppler transducer means, mounted on said transducer probe proximate to said transducer array, for receiving ultrasonic echos of the continuous ultrasonic wave which are reflected from the blood flow along a fixed, second beam which intersects said first beam at an intersection point within said blood flow;

scanning means, coupled with said transducer array, for selectively varying the direction of the said first beam to adjust the intersection point of said first and second beams and thereby adjust the depth of the intersection point within the subject;

processing means, coupled with said Doppler transducer means and said transducer array, for processing signals from said Doppler transducer and said transducer array to provide a signal indicative of the velocity of the blood flow within the subject at the intersection point; and indication means, coupled with said processing means, for providing an output of information indicative of the velocity of the blood flow within the subject at the intersection point.

9. The ultrasonic apparatus of claim 8 wherein said transducer array is a plural array having a single, central axis perpendicular to the array face and wherein said transducer array and said Doppler transducer are fixedly mounted on said transducer probe so that the single, central axis of the transducer array and the second, fixed beam of the Doppler transducer probe point in different directions.

10. The ultrasonic apparatus of claim 8 wherein said indication means includes displaying means for visually displaying the velocity of the blood flow.

11. The ultrasonic apparatus of claim 8 wherein said scanning means includes means for steering said first beam by controlling the timings of exciting the ultrasonic elements of said array.

12. The ultrasonic measuring apparatus of claim 8 wherein said scanning means includes means for translating said first beam by changing the ultrasonic elements of said array to be excited along the array.

13. The ultrasonic measuring apparatus of claim 8 wherein said sensing means includes a guadrature detector.

14. The ultrasonic apparatus of claim 13 wherein said sensing means further includes a fast Fourier transform analyzer.

15. An ultrasonic measuring apparatus for providing both a tomographic image and information concerning the blood flow of a living subject to be examined comprising:

a transducer probe for contact with the exterior surface of the subject;

a transducer array of ultrasonic transducer elements for transmitting ultrasonic pulses toward the subject along at least a variable, first beam, receiving echos reflected from the subject along at least the first beam, and converting the received echos into electrical signals representative of a tomographic image of the subject;

scanning means, coupled with said transducer array, for selectively varying the direction of said first beam;

means coupled with said transducer array, for processing the electrical signals from said transducer array and providing a tomographic image of the subject on a monitor;

Doppler transducer means, mounted on said transducer probe proximate to said transducer array, for transmitting a continuous wave toward the subject along a fixed, second beam for intersection with the first beam at a point within the blood flow of the subject, the intersection point depending upon the direction in which said first beam is pointed relative to second beam;

control means, coupled with said transducer array, for causing said transducer array to receive ultrasonic echos of the continuous ultrasonic wave which are reflected from the blood flow along the first beam the intersection point within said blood flow;

processing means, coupled with said transducer array and said Doppler transducer, for processing signals from said Doppler transducer and said transducer array to provide a signal indicative of the velocity of the blood flow within the subject at the intersection point; and indication means, coupled with said processing means, for providing information indicative of the velocity of the blood flow within the subject at the intersection point.

16. The ultrasonic measuring apparatus of claim 15 wherein said transducer array is a plural array having a single central axis perpendicular to the array face and wherein said transducer array and said Doppler transducer are fixedly mounted on said transducer probe so that the first, fixed beam of the Doppler transducer means and the single, central axis of the transducer array point in different directions.

17. The ultrasonic apparatus of claim 15 wherein said indication means includes displaying means for visually displaying the velocity of the blood flow.

18. The ultrasonic apparatus of claim 15 wherein said scanning means includes means for steering said first beam by controlling the timings of exciting the ultrasonic elements of said array.

19. The ultrasonic measuring apparatus of claim 15 wherein said scanning means includes means for translating said first beam by changing the ultrasonic elements of said array to be excited along the array.

20. The ultrasonic measuring apparatus of claim 15 wherein said sensing means includes a guadrature detector.

21. The ultrasonic apparatus of claim 20 wherein said sensing means further includes a fast Fourier transform analyzer.

* * * * *